United States Patent [19]

Nguyen

[11] 4,381,320
[45] Apr. 26, 1983

[54] NON-IONIC ABSORBENT POLYMERS

[75] Inventor: Hien V. Nguyen, East Windsor, N.J.

[73] Assignee: Johnson & Johnson, New Brunswick, N.J.

[21] Appl. No.: 270,166

[22] Filed: Jun. 3, 1981

[51] Int. Cl.³ .............................................. B05D 3/06
[52] U.S. Cl. .................................... 427/44; 128/284; 204/159.14; 428/913
[58] Field of Search ................ 427/44, 256, 280, 288; 204/159.14; 428/913, 284, 290 R, 287

[56] References Cited

U.S. PATENT DOCUMENTS

| | | |
|---|---|---|
| 3,664,343 | 5/1972 | Assarsson ........................ 204/159.14 |
| 3,898,143 | 8/1975 | Assarsson et al. ............. 204/159.14 |
| 3,900,378 | 8/1975 | Yen et al. ......................... 204/159.14 |
| 4,232,674 | 11/1980 | Melican .............................. 128/287 |

Primary Examiner—John H. Newsome
Attorney, Agent, or Firm—Charles J. Metz; Alice O. Robertson

[57] ABSTRACT

An absorbent material is produced by exposing an aqueous solution of polyvinyl alcohol and a low molecular weight, water soluble copolymer containing polymerized oxyethylene and oxypropylene units, to sufficient electromagetic or corpuscular ionizing radiation to form a gel.

11 Claims, No Drawings

NON-IONIC ABSORBENT POLYMERS

SPECIFICATION

The invention relates to absorbent polymers and to absorbent composites containing such polymers.

BACKGROUND OF THE INVENTION

Absorbent composites are widely employed as diapers, wound dressings, sanitary products, bandages, incontinent pads, and the like. A great deal of research has been performed in the last few years in attempting to produce new "superabsorbent" polymers. Superabsorbent polymers are generally considered to be hydrophilic polymers that swell when they contact water, but which are not soluble in water. Such polymers usually have the theoretical capacity to absorb at least 10 to 15 times their own weight in distilled or deionized water.

The present invention is based upon a discovery of a new absorbent polymer system that is relatively inexpensive to produce and, at the same time, has a suprisingly high capacity to absorb water and other aqueous fluids.

BRIEF SUMMARY OF THE INVENTION

The invention provides a process which comprises exposing an aqueous solution of polyvinyl alcohol and a low molecular weight, water-soluble copolymer containing polymerized oxyethylene and oxypropylene units, to electromagnetic or corpuscular ionizing radiation of sufficient dosage to form a gel.

The invention also provides the gelled product that is produced by the process of the invention.

THE PRIOR ART

Assarsson et al., in U.S. Pat. No. 3,957,605, discloses a process for co-cross-linking water soluble polymers. In this process, high molecular weight polyethylene oxide in aqueous solution along with another water soluble polymer, including polyvinyl alcohol, is subjected to ionizing radiation to produce a co-cross-linked product.

King, in U.S. Pat. No. 3,264,202, discloses the use of ionizing radiation to cross-link polyalkylene oxides.

Graham, in U.S. Pat. No. 2,964,455, discloses the electron beam irradiation of molten polymeric alkylene oxide.

DETAILED DESCRIPTION OF THE INVENTION

The two polymeric materials that are employed in the invention are polyvinyl alcohol and low molecular weight, water soluble, polyethylene oxide/polypropylene oxide copolymer. The polyvinyl alcohol that is employed is a relatively high molecular weight, water-soluble material that is well known in the art. Such materials are commercially available in varying degrees of hydrolysis and in varying molecular weights. The essential characteristic is that the polyvinyl alcohol be water soluble. Usually, the molecular weight will be above about 40,000.

The ethylene oxide/propylene oxide copolymers that are employed in the invention are low molecular weight materials that are water soluble. They have molecular weights of up to about 12,000, preferably below about 10,000, more preferably below about 8,000, and down to about 2,000. The ratio of ethylene oxide to propylene oxide in the copolymer is such that it is water soluble.

As a general rule, the copolymer will have from about 50 weight percent to about 85 weight percent of polymerized ethylene oxide units, with the remainder being polymerized propylene oxide units. The copolymers are generally linear.

The two polymers are employed in aqueous solution. The polymers are used in proportions or amounts up to the limit of solubility or compatibility of the two polymers. Total solution concentrations of up to about 4 or 5 weight percent have been found acceptable. At higher concentrations, compatibility problems may appear. Preferred total solution concentrations are from about 0.5 to 4 weight percent. The ratio of the two polymers is not narrowly critical, and can vary, for instance, from about ½ to about 10 parts by weight of copolymer per part of polyvinyl alcohol. Preferably, the proportion of polyvinyl alcohol is kept as low as possible.

The aqueous solution of the two polymers is subjected to sufficient electromagnetic or corpuscular ionizing radiation such as accelerated electrons, gamma rays, or the like, sufficient to cross-link the two polymers and form a gel (as used herein, "gel" refers to a composition comprising a water-swellable, water-insoluble polymer, swollen with water). The dose employed in particular cases will vary somewhat, depending on factors such as degree of cross-linking desired, voltage and sample thickness when accelerated electrons are used, and the like. In general, it is desired to irradiate with doses in excess of about two megarads, and preferably in excess of about three megarads. Particularly when using lower doses, it may be desirable to purge oxygen from the solution (as by bubbling nitrogen through the solution).

Accelerated electrons is the preferred type of irradiation to employ.

In one preferred aspect of the invention, the aqueous solution of polymers is applied to a fibrous substrate prior to irradiation. The fibrous substrate can be a loosely formed batt of fibers, or it can be an already formed fibrous material such as paper, a nonwoven fabric, or a woven fabric such as cotton gauze or a knitted fabric. It is generally preferred to employ absorbent fibers in the fibrous substrate such a cellulosic fibers including woodpulp, rayon, and cotton. It is permissible, however, to include other types of fibers in the fibrous substrate.

The aqueous solution is applied to the fibrous substrate in a predetermined pattern. It is preferred to employ an intermittent pattern such as fine dots, intermittent stripes, or the like. The pattern can be employed to produce "dams", "wicking channels," or the like, in an absorbent composite that is produced by irradiating the aqueous mixture of polymers on a fibrous substrate. For instance, a diaper having a continuous stripe of cross-linked absorbent polymer around the edges of the absorbent padding portion of the diaper will have less tendency to leak around the edges. In general, it is preferred to employ a pattern of very finely divided discreet areas in order to provide as high a ratio of polymer surface area to mass as possible. The reason for this is to utilize the absorbent capacity of the polymer to the fullest extent possible.

The aqueous solution can be applied to the fibrous substrate in the predetermined pattern by conventional means such as gravure printing, spraying, or the like.

If desired, the aqueous solution can be applied to the fibrous substrate in an overall pattern, which may be applied in an amount sufficient to simply coat one surface of the fibrous substrate or it can be employed in a quantity sufficient to penetrate as much of the thickness of the fibrous substrate as is desired in particular cases.

After the aqueous solution of the two polymers has been subjected to electromagnetic or corpuscular ionizing radiation, to form a gel (which comprises the water-swellable composition of the invention swollen with water), the gel can be dried in order to form a water-swellable, water-insoluble product. This can be done by conventional procedures such as by exposing the aqueous gel to elevated temperature. Since polyvinyl alcohol is relatively temperature sensitive, the polymers should not be heated to temperatures much in excess of about 80° C., especially after most of the water has been removed from the aqueous gel.

In the Examples, the following materials were used:

I. Ethylene oxide/Propylene oxide "EtO/PrO" copolymers

|  | EtO/PrO Weight Ratio | Molecular Weight |
|---|---|---|
| Copolymer A | 50/50 | 2,600 |
| Copolymer B | 70/30 | 2,500 |
| Copolymer C | 70/30 | 4,400 |
| Copolymer D | 75/25 | 11,000 |

II. Polyvinyl Alcohol "PVA"

|  | Molecular Weight | Degree of Hydrolysis |
|---|---|---|
| PVA-A | 185,000 | 100 |
| PVA-B | 45,000 | 100 |

EXAMPLES 1-2 AND CONTROL EXAMPLES 1-7

Aqueous solutions of the polymers shown in Table I were exposed to the indicated dose of gamma radiation. The solutions were first purged with nitrogen to remove oxygen. Table I displays the solutions irradiated and the dose required to form a gel in those cases where a gel could be produced:

TABLE I

|  | Polymer(s) | Concentration[1] | Radiation Dose, MRad, or Comment |
|---|---|---|---|
| Example |  |  |  |
| 1 | 80 Copolymer D[2] 20 PVA-B | 2 | 2 |
| 2 | 75 Copolymer B 25 PVA-B | 2 | 16 |
| Control Example |  |  |  |
| 1 | Copolymer A | 2 | no gel |
| 2 | Copolymer B | 2 | no gel |
| 3 | Copolymer C | 2 | no gel |
| 4 | Copolymer D | 2 | no gel |
| 5 | Copolymer D | 68 | sticky mass |
| 6 | Copolymer D | 8-30 | 14 |
| 7 | PVA-B | 0.5 | 0.5-0.6 |

[1]Total concentration of polymer(s) in water, weight percent
[2]Proportions are by weight Copolymers A, B, and C, when irradiated in the absence of polyvinyl alcohol, would not form a gel at any concentration. The higher molecular weight copolymer D forms a gel when irradiated at higher concentrations, but this gelled material is very difficult to dry under conditions that do not cause heat degradation of the cross-linked polymer.

The gelled and dried material of Examples 1 and 2 were tested and found to swell when contacted with water. Their absorbent capacities are about 13 milliliters per gram. In contrast, dried irradiated polyvinyl alcohol, as illustrated by Control Example 7, has been found not to readily swell when contacted with water and to have an absorbent capacity of only about 7 milliliters per gram.

Absorbent capacity, as used herein, is the weight of deionized or distilled water absorbed per gram of sample, as measured by a gravimetric absorbency tester ("GAT"), using a point source with the sample held on a horizontal plate. The sample is unloaded, i.e., no compression load is held on the sample. The GAT is described in detail in commonly assigned U.S. patent application Ser. No. 149,214, filed on May 12, 1980. Briefly, the GAT is an apparatus for determining the weight of liquid flowing to or from a test site. The apparatus comprises, in combination:

A vessel for containing liquid, said vessel being supported solely by weighing means;

Indicating means for indicating the weight sensed by said weighing means;

A test surface to receive a specimen to be tested, said test surface including said test site;

Conduit means operatively connecting said vessel to said test site for directing a flow of liquid between said vessel and said test site; and Means for vertically positioning said test site.

EXAMPLE 3

An aqueous solution containing 3.2 weight percent Copolymer D and 0.8 weight percent PVA-B was added to a suction bonded rayon/wood pulp nonwoven fabric and to a cotton gauze fabric, by dipping each fabric into the solution. Add-ons, on a solids basis, were 35 percent and 37.5 percent, respectively. Samples of each fabric were exposed to accelerated electrons at doses of 3, 5 and 8 megarads. An "ICT" (Insulating Core Transformer) accelerator capable of providing a voltage of 500,000 volts was employed. In all cases, the solution was transformed into gels.

When dried, the fabrics containing the water-swellable, water-insoluble materials, are useful as pads for absorbing aqueous liquids.

EXAMPLES 4 AND 5

Two aqueous solutions, one containing 0.5 weight percent PVA-A and 3.5 weight percent Copolymer A, and the other containing 0.5 weight percent PVA-A and 3.5 weight percent Copolymer C, are gravure printed on continuous webs of a print-bonded rayon nonwoven fabric weighing 600 grams per square yard, and made in accordance with the general teachings of U.S. Pat. Nos. 3,705,687 and 2,705,688. The printing of the solutions is done by a process analogous to that described by Drelich in U.S. Pat. No. 4,084,033. The print roll contains a pattern of spaced, fine, round depressions about 0.02 inches deep and 0.05 inches in diameter, six depressions to the inch in each direction in an alternating pattern. The add-on (solids basis) is about 10 weight percent.

The printed fabrics are exposed to accelerated electrons from a Dynamitron accelerator capable of providing a voltage of 800 KV. The doses in each case are 4 megarads. The webs are then passed over drying cans to remove the water from the treated webs. The resulting fabrics containing the water-swellable, water-insoluble products in an intermittent pattern of fine dots are useful as absorbent pads for absorbent products such as incontinent pads.

What is claimed is:

1. Process which comprises exposing an aqueous solution of polyvinyl alcohol and a low molecular weight, water-soluble copolymer containing polymerized oxyethylene and oxypropylene units to electromagnetic or corpuscular ionizing radiation of sufficient dosage to form a gel, wherein the molecular weight of said copolymer is below about 12,000.

2. Process of claim 1 wherein said gel is dried to form a water-swellable, water-insoluble product.

3. Process of claim 1 wherein said aqueous solution is applied to a fibrous substrate prior to irradiation.

4. Process of claim 3 wherein the solution is applied to the fibrous substrate in an intermittent pattern.

5. Process of claim 1, 2, 3, or 4 wherein from about ½ to about 10 parts, by weight, of said copolymer are employed per part, by weight, of polyvinyl alcohol.

6. Process of claim 5 wherein the concentration of said copolymer plus polyvinyl alcohol in said aqueous solution is from about 0.5 to about 4 weight percent, based on total solution weight.

7. The process of claim 1, 2, 3 or 4 wherein said radiation is accelerated electrons.

8. The process of claim 5 wherein said radiation is accelerated electrons.

9. The product produced by the process of claim 1.

10. The product produced by the process of claim 2.

11. The product produced by the process of claim 3.

* * * * *